(12) United States Patent
Hashimoto et al.

(10) Patent No.: US 9,248,432 B2
(45) Date of Patent: Feb. 2, 2016

(54) TITANIUM OXIDE PHOTOCATALYST HAVING COPPER COMPOUNDS SUPPORTED THEREON, AND METHOD FOR PRODUCING SAME

(75) Inventors: Kazuhito Hashimoto, Tokyo (JP); Masahiro Miyauchi, Tokyo (JP); Xiaoqing Qiu, Tokyo (JP); Kayano Sunada, Tokyo (JP); Yasushi Kuroda, Toyama (JP); Yasuhiro Hosogi, Toyama (JP); Ding Li, Toyama (JP); Yoshiki Shimodaira, Chiba (JP)

(73) Assignees: THE UNIVERSITY OF TOKYO, Tokyo (JP); SHOWA DENKO K.K., Tokyo (JP)

( * ) Notice: Subject to any disclaimer, the term of this patent is extended or adjusted under 35 U.S.C. 154(b) by 259 days.

(21) Appl. No.: 13/882,425

(22) PCT Filed: Jun. 22, 2012

(86) PCT No.: PCT/JP2012/066054
§ 371 (c)(1),
(2), (4) Date: Jul. 11, 2013

(87) PCT Pub. No.: WO2013/002151
PCT Pub. Date: Jan. 3, 2013

(65) Prior Publication Data
US 2013/0281283 A1 Oct. 24, 2013

(30) Foreign Application Priority Data

Jun. 27, 2011 (JP) ................. 2011-142341

(51) Int. Cl.
| | |
|---|---|
| *B01J 23/72* | (2006.01) |
| *A01N 59/20* | (2006.01) |
| *B01J 21/06* | (2006.01) |
| *B01J 35/00* | (2006.01) |
| *B01J 37/06* | (2006.01) |
| *B01J 37/16* | (2006.01) |
| *B01J 37/34* | (2006.01) |
| *B01J 37/00* | (2006.01) |
| *C09C 1/36* | (2006.01) |
| *B01J 37/04* | (2006.01) |
| *B01J 35/10* | (2006.01) |
| *B82Y 30/00* | (2011.01) |
| *B01J 37/03* | (2006.01) |
| *B01J 37/08* | (2006.01) |

(52) U.S. Cl.
CPC ............ *B01J 23/72* (2013.01); *A01N 59/20* (2013.01); *B01J 21/063* (2013.01); *B01J 35/002* (2013.01); *B01J 35/004* (2013.01); *B01J 35/1014* (2013.01); *B01J 37/0009* (2013.01); *B01J 37/04* (2013.01); *B01J 37/06* (2013.01); *B01J 37/16* (2013.01); *B01J 37/344* (2013.01); *B82Y 30/00* (2013.01); *C09C 1/3653* (2013.01); *B01J 37/035* (2013.01); *B01J 37/08* (2013.01); *C01P 2002/80* (2013.01); *C01P 2004/64* (2013.01); *C01P 2006/12* (2013.01)

(58) Field of Classification Search
CPC ...... B01J 23/72; B01J 35/1014; B01J 35/002; B01J 35/004; B01J 37/04; B01J 37/06; B01J 37/344; B01J 37/16; B01J 37/0009; B01J 37/035; B01J 37/08; B01J 21/063; B82Y 30/00; C09C 1/3653; A01N 59/20; C01P 2004/64; C01P 2002/80; C01P 2006/12
See application file for complete search history.

(56) References Cited

U.S. PATENT DOCUMENTS

| | | | |
|---|---|---|---|
| 5,853,866 A | 12/1998 | Watanabe et al. | |
| 7,449,166 B2 * | 11/2008 | Tanaka et al. | 423/610 |
| 2013/0344124 A1 * | 12/2013 | Hashimoto et al. | 424/419 |

FOREIGN PATENT DOCUMENTS

| | | |
|---|---|---|
| JP | 8-66635 A | 3/1996 |
| JP | 2003-251195 A | 9/2003 |
| JP | 2004-143032 A | 5/2004 |
| JP | 2006-232729 A | 9/2006 |
| JP | 2006-346651 A | 12/2006 |
| JP | 2007-51263 A | 3/2007 |
| JP | 2009-056348 A | 3/2009 |
| JP | 2011-63473 A | 3/2011 |
| JP | 2011-79713 A | 4/2011 |

(Continued)

OTHER PUBLICATIONS

Hiroshi Irie et al.; "Efficient visible light-sensitive photocatalysts: Grafting Cu(II) ions onto $TiO_2$ and $WO_3$ photocatalysts"; Chemical Physics Letters; vol. 457, No. 1-3; May 20, 2008; pp. 202-205; XP022669975.

(Continued)

*Primary Examiner* — Anthony J Zimmer
(74) *Attorney, Agent, or Firm* — Sughrue Mion, PLLC (57) ABSTRACT

A copper compound-carried titanium oxide photocatalyst which is excellent in a photocatalytic activity and a viral inactivation property and a production process for the same can be provided by a copper compound-carried titanium oxide photocatalyst comprising titanium oxide in which a content of rutile type titanium oxide is 50% by mole or more and a monovalent copper compound and a divalent copper compound which are carried on a surface of the titanium oxide described above and a production process for a copper compound-carried titanium oxide photocatalyst, comprising a step of carrying a monovalent copper compound and a divalent copper compound on a surface of titanium oxide in which a content of rutile type titanium oxide is 50% by mole or more.

9 Claims, 5 Drawing Sheets (56) References Cited

FOREIGN PATENT DOCUMENTS

| JP | 2011-111600 A | | 6/2011 |
|---|---|---|---|
| JP | 2011-153163 A | | 8/2011 |
| JP | 2012-16697 A | | 1/2012 |
| WO | 2011/043496 A2 | | 4/2011 |
| WO | WO 2011078203 A1 | * | 6/2011 |
| WO | 2012/033071 A1 | | 3/2012 |

OTHER PUBLICATIONS

C. Karunakaran et al.; "Cu-doped $TiO_2$ nanoparticles for photocatalytic disinfection of bacteria under visible light"; Journal of Colloid and Interface Science; vol. 352, No. 1; Dec. 1, 2010; pp. 68-74; XP027307764.

Bin Ql et al.; "Low-temperature and one-step synthesis of rutile $TiO_2$ aqueous sol by heterogeneous nucleation method"; Journal of Colloid and Interface Science; vol. 345, No. 2; May 1, 2010; pp. 181-186; XP055088653.

Extended European Search Report dated Dec. 6, 2013 for corresponding EP Application No. 12804801.4.

* cited by examiner

TITANIUM OXIDE PHOTOCATALYST HAVING COPPER COMPOUNDS SUPPORTED THEREON, AND METHOD FOR PRODUCING SAME

BACKGROUND OF THE INVENTION

The present invention relates to a copper compound-carried titanium oxide photocatalyst having a copper compound on a surface of titanium oxide and a production process for the same.

RELATED ART

Photocatalysts prepared by using titanium oxide are widely used as a photocatalyst because of the reasons that they are inexpensive and excellent in a chemical stability and have a high catalytic activity and that they are harmless to human bodies (refer to, for example, patent documents 1 and 2).

However, titanium oxide exerts a photocatalytic activity only by irradiation with a UV ray, and therefore it cannot exert a sufficiently high catalytic activity under an indoor light scarcely containing a UV component. Accordingly, visible light-response type photocatalysts exerting a photocatalytic activity even under an indoor light such as a fluorescent lamp and the like have been proposed.

Titanium dioxide in which atoms such as nitrogen, carbon, sulfur and the like are doped into a crystal lattice is described in, for example, a patent document 3 as the above visible light response type photocatalyst. Also, a deactivator for phage virus comprising anatase type titanium oxide containing copper in a range of $CuO/TiO_2$ (mass % ratio)=1.0 to 3.5 is described in a patent document 4.

PATENT DOCUMENTS

Patent document 1: JP-A 2007-51263
Patent document 2: JP-A 2006-346651
Patent document 3: JP-A 2004-143032
Patent document 4: JP-A 2006-232729

SUMMARY OF THE INVENTION

In the visible light-response type photocatalyst described above, a viral inactivation property (hereinafter referred to an antiviral property) and a photocatalytic activity are desired to be further improved.

That is, a visible light-response type photocatalyst in which atoms such as nitrogen and the like are doped into a crystal lattice of titanium oxide as shown in the patent document 3 is limited in a doping amount thereof, and therefore it is limited in an improvement of a photocatalytic activity. Further, it is short of a viral inactivation property.

Also in a visible light response type photocatalyst comprising anatase type titanium oxide containing divalent copper as shown in the patent document 4, a viral inactivation property is not sufficiently high, and a photocatalytic activity cannot sufficiently be enhanced as well.

The present invention has been made under the above situations, and an object thereof is to provide a copper compound-carried titanium oxide photocatalyst which has a visible light responsiveness (performance to exert a photocatalytic activity even under an indoor light such as a fluorescent lamp and the like) and which is excellent in a viral inactivation property and a photocatalytic activity, and a production process for the same.

Investigations repeated by the present inventors in various manners in order to achieve the objects described above have resulted in finding that a copper compound-carried titanium oxide photocatalyst which is excellent in a viral inactivation property (antiviral property) and a photocatalytic activity can be provided by a copper compound-carried titanium oxide photocatalyst having a copper compound on a surface of titanium oxide, wherein titanium oxide in which a content of rutile type titanium oxide is 50% by mole or more is used as the titanium oxide, and a monovalent copper compound is used as the copper compound together with a divalent copper compound. The present invention has been completed based on the above knowledge.

That is, the present invention provides the following items [1] to [10].

[1] A copper compound-carried titanium oxide photocatalyst comprising titanium oxide in which a content of rutile type titanium oxide is 50% by mole or more and a monovalent copper compound and a divalent copper compound which are carried on a surface of the titanium oxide described above.

[2] The copper compound-carried titanium oxide photocatalyst according to the above item [1], wherein an abundance ratio of monovalent copper to a sum of monovalent copper and divalent copper is 20 to 70% by mole.

[3] The copper compound-carried titanium oxide photocatalyst according to the above item [1] or [2], wherein the monovalent copper compound contains copper (I) oxide.

[4] The copper compound-carried titanium oxide photocatalyst according to any one of the above items [1] to [3], wherein the divalent copper compound contains copper (II) hydroxide.

[5] The copper compound-carried titanium oxide photocatalyst according to any one of the above items [1] to [4], wherein the titanium oxide described above is obtained by a vapor phase method.

[6] A production process for a copper compound-carried titanium oxide photocatalyst, comprising a step of carrying a monovalent copper compound and a divalent copper compound on a surface of titanium oxide in which a content of rutile type titanium oxide is 50% by mole or more.

[7] The production process for a copper compound-carried titanium oxide photocatalyst according to the above item [6], comprising a step of adding a reducing agent for reducing divalent copper to monovalent copper to a suspension prepared by blending the divalent copper compound with the titanium oxide in which a content of rutile type titanium oxide is 50% by mole or more.

[8] The production process for a copper compound-carried titanium oxide photocatalyst according to the above item [6], comprising a step of irradiating a catalyst precursor containing the titanium oxide in which a content of rutile type titanium oxide is 50% by mole or more and the divalent copper compound carried on a surface of the titanium oxide described above with light to reduce a part of the divalent copper compound to the monovalent copper compound.

[9] The production process for a copper compound-carried titanium oxide photocatalyst according to the above item [8], wherein the irradiation with light described above is carried out in an alcohol-containing atmosphere.

[10] The production process for a copper compound-carried titanium oxide photocatalyst according to any one of the above items [6] to [9], wherein the titanium oxide described above is obtained by a vapor phase method.

According to the present invention, a copper compound-carried titanium oxide photocatalyst which is excellent in a viral inactivation property (antiviral property) and a photocatalytic activity and a production process for the same can be provided.

MODE FOR CARRYING OUT THE INVENTION

Copper Compound-Carried Titanium Oxide Photocatalyst:

The copper compound-carried titanium oxide photocatalyst of the present invention comprises titanium oxide in which a content of rutile type titanium oxide is 50% by mole or more and a monovalent copper compound and a divalent copper compound which are carried on a surface of the titanium oxide described above.

According to the copper compound-carried titanium oxide photocatalyst of the present invention, it is excellent in a photocatalytic activity exerted by a visible light since the divalent copper compound is carried on a surface of the titanium oxide.

That is, titanium oxide simple substance produces electrons and holes by photoexcitation brought about by irradiation with a UV ray. Oxygen which is present in air and water and adsorbed on a surface of titanium oxide is subjected to one-electron reduction by the above resulting electrons as shown in the following formula (1):

$$O_2 + H^+ + e^- \rightarrow HO_2 \; (-0.046 \text{ V vs. SHE, pH}=0) \quad (1)$$

In Formula (1), SHE means a standard hydrogen electrode; vs. SHE means that an electrical potential is measured based on SHE; and pH=0 means that all of an activity of hydrogen gas and an activity of hydrogen ions are 1.

The resulting reaction (1) described above makes it possible to separate the electrons and the holes produced by the photoexcitation described above and prevent both from being recombined and makes it possible to oxidize and decompose organic substances by a strong oxidizing power and a high mobility of the holes. As shown above, in order to subject oxygen of titanium oxide to one-electron reduction, the electrons have to be photoexcited up to a high position of $-0.046$ V (pH=0) which is an oxidation-reduction potential thereof.

In contrast with this, in copper-carried titanium oxide carried on a surface of titanium oxide with a copper compound, divalent copper can be reduced by photoexciting electrons in the titanium oxide by a visible light up to +0.16 V (pH=0) which is an oxidation-reduction potential of a copper ion without photoexciting electrons up to such a high position as described above. Subsequently, monovalent copper reduces oxygen according to the following formulas (2) and (3), and the monovalent copper itself returns to the divalent copper to thereby make it possible to separate the electrons and the holes and prevent both from being recombined. The above holes have a strong oxidizing power and a high mobility as is the case with conventional titanium oxide and therefore can oxidize and decompose organic substances.

$$O_2 + 2H^+ + 2e^- \rightarrow H_2O_2 \; (+0.068 \text{ V vs. SHE, pH}=0) \quad (2)$$

$$O_2 + 4H^+ + 4e^- \rightarrow 2H_2O \; (+1.23 \text{ V vs. SHE, pH}=0) \quad (3)$$

Also, the copper compound-carried titanium oxide photocatalyst of the present invention contains both of the monovalent copper compound and the divalent copper compound and therefore is excellent in both of a viral inactivation property and a photocatalytic activity. That is, the copper compound-carried titanium oxide photocatalyst of the present invention contains the monovalent copper compound which is more excellent in a viral inactivation property than the divalent copper compound, and therefore it is excellent in a viral inactivation property. Also, the copper compound-carried titanium oxide photocatalyst of the present invention contains the foregoing divalent copper compound required for a photocatalytic activity exerted by a visible light, and therefore it is excellent in a photocatalytic activity exerted by a visible light. In this connection, the copper compound-carried titanium oxide photocatalyst of the present invention exerts as well such a photocatalytic activity as described above by a UV ray.

Further, the copper compound-carried titanium oxide photocatalyst of the present invention comprises rutile type titanium oxide as a principal component of the titanium oxide, and therefore it is excellent in a viral inactivation property and a photocatalytic activity as compared with a case in which it comprises anatase type titanium oxide and brookite type titanium oxide as a principal component. A reason therefor is not clear, and it is estimated to be due to that the foregoing oxidation-reduction reaction between the monovalent copper and the divalent copper is carried out more efficiently under the presence of the rutile type titanium oxide.

In this regard, the photocatalytic activity means at least one selected from a photoinduced degradability and a photoinduced hydrophilic property. The photoinduced degradability is an action to oxidize and decompose organic substances adsorbed on a surface treated with titanium oxide, and the photoinduced hydrophilic property is an action to provide a surface treated with titanium oxide with a hydrophilicity in which the surface is liable to be compatible with water. The above photoinduced hydrophilic property is considered to be brought about by hydroxyl groups on a surface of titanium oxide which are increased by holes produced and diffused by photoexcitation.

Also, virus means DNA virus and RNA virus and includes as well bacteriophage (hereinafter abbreviated as "phage") which is virus infected with bacteria.

Next, the respective components of the copper compound-carried titanium oxide photocatalyst shall be explained.

<Titanium Oxide>

The titanium oxide in the copper compound-carried titanium oxide photocatalyst described above contains a large amount of rutile type titanium oxide, and therefore it is excellent in a viral inactivation property (antiviral property) and a photocatalytic activity.

A content of the rutile type titanium oxide based on a whole amount of the titanium oxide is 50% by mole or more. If it is less than 50% by mole, the photocatalyst is inferior in a photocatalytic activity and a viral inactivation property. From the above viewpoint, a content of the rutile type titanium oxide is preferably 50% by mole or more, more preferably 70% by mole or more, further preferably 80% by mole or more and particularly preferably 85% by mole or more.

A specific surface area of the titanium oxide is preferably 1 to 200 $m^2/g$. If it is 1 $m^2/g$ or more, the photocatalyst has a large specific surface area and therefore is excellent in a photocatalytic activity. If it is 200 $m^2/g$ or less, the photocatalyst is excellent in a handling property. From the above viewpoints, a specific surface area of the titanium oxide is preferably 1 $m^2/g$, more preferably 3 $m^2/g$, further preferably 4 $m^2/g$ and further more preferably 8 $m^2/g$ in terms of a lower limit value, and it is preferably 200 $m^2/g$, more preferably 100 $m^2/g$, further preferably 70 $m^2/g$ and further more preferably 50 $m^2/g$ in terms of an upper limit value. Also, a specific surface area of the titanium oxide is more preferably 3 to 100 $m^2/g$, further preferably 4 to 70 $m^2/g$ and particularly preferably 8 to 50 $m^2/g$. In this regard, the specific surface area is a value measured by a BET method carried out by nitrogen adsorption.

The titanium oxide is obtained preferably by a vapor phase method (a method for obtaining titanium oxide by a vapor phase reaction of titanium tetrachloride with oxygen) using titanium tetrachloride as a raw material. Titanium oxide obtained by the vapor phase method has a uniform particle diameter, and in addition thereto, it has a high crystallinity since it has passed through a high temperature process in production. The above characteristics are suitable when the above titanium oxide is used for a photocatalyst.

Commercially available titanium oxide is advantageously used as it is for the titanium oxide taking a step of preparing the catalyst into consideration. For example, when titanium oxide having a large specific surface area and a low rutile crystallinity among commercially available titanium oxides is used, it has to be subjected to burning treatment and the like to obtain titanium oxide having an optimum specific surface area and an optimum crystallinity. If passing through such a step of burning, the above step itself requires additional time and labor to result in elevating the cost. Further, the trouble that titanium oxide is colored in burning is likely to be brought about. From the above viewpoints, commercially available products (rutile type titanium oxide F-10 and the like, manufactured by Showa Titanium K.K.) of titanium oxide which has a suitable crystallinity and a suitable specific surface area and which is obtained by a vapor phase method are preferably used as they are.

<Copper Compound>

The copper compound-carried titanium oxide photocatalyst of the present invention has the monovalent copper compound and the divalent copper compound on a surface of the titanium oxide. The above matter allows the copper compound-carried titanium oxide photocatalyst of the present invention to be excellent, as described above, in a viral inactivation property (antiviral property) and excellent as well in a photocatalytic activity exerted by a visible light and a UV ray.

A content of the copper compound based on the titanium oxide is preferably 0.01 to 10 parts by mass in terms of copper ions (sum of monovalent copper ions and divalent copper ions) based on 100 parts by mass of the titanium oxide. If it is 0.01 part by mass or more, the antiviral effect and the visible light responsiveness are exerted well by carrying the copper compound. If it is 10 parts by mass or less, a surface of the titanium oxide is prevented from being coated, and a function of the photocatalyst is exerted well. From the above viewpoints, a content of the copper ions is preferably 0.01 part by mass, more preferably 0.05 part by mass, further preferably 0.07 part by mass and further more preferably 0.1 part by mass in terms of a lower limit value based on 100 parts by mass of the titanium oxide, and it is preferably 10 parts by mass, more preferably 7 parts by mass, further preferably 5 parts by mass and further more preferably 2 parts by mass in terms of an upper limit value based on 100 parts by mass of the titanium oxide. Also, a content of the copper ions is more preferably 0.05 to 7 parts by mass, further preferably 0.07 to 5 parts by mass and particularly preferably 0.1 to 2 parts by mass based on 100 parts by mass of the titanium oxide.

An average particle diameter of the copper compound carried on the titanium oxide is preferably 0.5 to 100 nm. If it is 0.5 nm or more, the copper compound is improved in a crystallinity and enhanced in antiviral property. If it is 100 nm or less, provided are the effects that (i) the copper compound is increased in a specific surface area and excellent in an antiviral property and that (ii) the copper compound can be carried well on a surface of the titanium oxide. From the above viewpoints, an average particle diameter of the copper compound is more preferably 0.5 to 80 nm, further preferably 1 to 70 nm and particularly preferably 2 to 50 nm. The above average particle diameters can be confirmed by observing them under an electron microscope.

An abundance ratio of the monovalent copper (Cu(I)) to a sum of the monovalent copper (Cu(I)) and the divalent copper (Cu(II)) is preferably 20 to 70% by mole. If it is 20% by mole or more, the copper compound is excellent in a viral inactivation property (antiviral property). If it is 70% by mole or less, an amount of the divalent copper (Cu(II)) is relatively increased, and the copper compound is excellent in a photocatalytic activity. From the above viewpoints, the abundance ratio described above is preferably 20% by mole, more preferably 25% by mole in terms of a lower limit value, and it is preferably 70% by mole, more preferably 60% by mole, further preferably 45% by mole and further more preferably 35% by mole in terms of an upper limit value. The above abundance ratio is more preferably 25 to 60% by mole, further preferably 25 to 45% by mole and particularly preferably 25 to 35% by mole.

<<Monovalent Copper Compound>>

The monovalent copper compound shall not specifically be restricted and includes at least one of copper (I) oxide, copper (I) sulfide, copper (I) iodide, copper (I) chloride and copper (I) hydroxide, and particularly copper (I) oxide is suitably used.

<<Divalent Copper Compound>>

The divalent copper compound shall not specifically be restricted and includes at least one of copper (II) hydroxide, copper (II) oxide, copper (II) chloride, copper (II) acetate, copper (II) sulfate, copper (II) nitrate, copper (II) fluoride, copper (II) iodide and copper (II) bromide, and particularly copper (II) hydroxide ($Cu(OH)_2$) is suitably used.

The monovalent copper compound and the divalent copper compound which are carried on the titanium oxide contain preferably copper (I) oxide and copper (II) hydroxide, and they consist preferably as well of copper (I) oxide and copper (II) hydroxide. Also, the monovalent copper compound and the divalent copper compound which are carried on the titanium oxide contain copper (I) oxide and copper (II) hydroxide, and a proportion of copper (I) oxide and copper (II)

hydroxide based on a whole amount of the monovalent copper compound and the divalent copper compound which are carried on the titanium oxide is preferably 80% by mass or more, more preferably 90% by mass or more, further preferably 95% by mass or more and further more preferably 100% by mass.

<<Copper Compound-Carried Titanium Oxide Photocatalyst>>

In the copper compound-carried titanium oxide photocatalyst of the present invention, a content of the rutile type titanium oxide is preferably 80% by mole or more, and an abundance ratio of the monovalent copper (Cu(I)) to a sum of the monovalent copper (Cu(I)) and the divalent copper (Cu (II)) is preferably 20 to 70% by mole.

Production Process for Copper Compound-Carried Titanium Oxide Photocatalyst:

In a production process for the copper compound-carried titanium oxide photocatalyst of the present invention, the monovalent copper compound and the divalent copper compound are carried on a surface of titanium oxide in which a content of rutile type titanium oxide is 50% by mole or more.

Next, the examples of the production process for the copper compound-carried titanium oxide photocatalyst of the present invention shall be explained.

<First Production Example>

In the present production example, a reducing agent for reducing divalent copper (Cu(II)) to monovalent copper (Cu (I)) is added to a suspension prepared by blending the divalent copper compound with the titanium oxide in which a content of rutile type titanium oxide is 50% by mole or more.

<<Step of Preparing Suspension>>

In the present step, the divalent copper compound is blended with the titanium oxide in which a content of rutile type titanium oxide is 50% by mole or more to prepare a suspension. After blending them as described above, the mixture is preferably stirred at, for example, 60° C. or higher, preferably 70 to 100° C. and more preferably 80 to 95° C. for several hours, preferably about 1 hour to prepare the suspension.

Titanium Oxide:

Various characteristics (a content of rutile type titanium oxide based on a whole amount of the titanium oxide and a specific surface area thereof) of the titanium oxide used in the present production examples are the same as described in the explanations of the copper compound-carried titanium oxide photocatalyst described above.

Divalent Copper Compound:

The divalent copper compound added is preferably at least one selected from copper (II) chloride, copper (II) sulfate, copper (II) nitrate and copper (II) acetate. It contains more preferably copper (II) chloride and consists further preferably of copper (II) chloride.

<<Step of Adding Reducing Agent>>

Next, the reducing agent for reducing the divalent copper (Cu(II)) to the monovalent copper (Cu(I)) is added to the suspension described above.

Capable of being used as the reducing agent is, for example, at least one substance selected from the group consisting of alkali metals, alkaline earth metals, aluminum, zinc, amalgams of alkali metals and zinc, hydrides of boron and aluminum, metal salts staying in a low oxidation state, hydrogen sulfide, sulfides, thiosulfates, oxalic acid, formic acid, ascorbic acid, substances having an aldehyde bond, alcohol compounds including phenol and the like. Preferably, the substances having an aldehyde bond can be used as the reducing agent. For example, sugars, more preferably glucose can be used as the substances having an aldehyde bond, but they shall not be restricted to the above substances. The sugars are the preferred reducing agent since they are inexpensive and free of a toxicity and can readily be removed by conventional operations such as washing and the like after the reductive reaction.

In the reducing treatment, the reaction is carried out after controlling the suspension containing the divalent copper compound and the titanium oxide to a basic. In the above case, a controlling agent for pH shall not specifically be restricted, and capable of being used is, for example, at least one selected from sodium hydroxide, potassium hydroxide, tetramethylammonium hydroxide, tetrabutylammonium hydroxide, triethylamine, trimethylamine, ammonia and basic surfactants (for example, BYK-9077 and the like, manufactured by BYK Chemie A.G.). At least one selected from sodium hydroxide and potassium hydroxide can suitably be used, and sodium hydroxide can more suitably be used.

The specific examples of a step of adding the reducing agent include, for example, a step in which sodium hydroxide ($NaOH/Cu^{2+}$=0 to 8 (mole ratio)) and sugars (for example, glucose and the like: sugars/$Cu^{2+}$=2 to 5 (mole ratio)) are added to the suspension described above. Then, the solution is stirred on the condition of pH 9 or higher at, for example, 60° C. or higher, preferably 65 to 95° C. for several hours, preferably about 1 hour, and the resulting solid matter is obtained by filtering, washed with water and then dried. Thus, capable of being prepared is the copper compound-carried titanium oxide photocatalyst in which the monovalent copper compound and the divalent copper compound are carried on a surface of the titanium oxide.

The copper compound-carried titanium oxide photocatalyst obtained by the above reaction comprises composite particles in which the monovalent copper compound and the divalent copper compound are carried on a surface of the titanium oxide particles, and it is provided with a viral inactivation property and a photocatalytic activity in combination.

In the above suspension, the divalent copper (II) contains preferably copper chloride; the reducing agent contains preferably sugars; and the pH controlling agent contains preferably sodium hydroxide. Further, the divalent copper (II) consists preferably of copper chloride; the reducing agent consists preferably of glucose; and the pH controlling agent consists preferably of sodium hydroxide.

<Second Production Example>

The present production example comprises a step of irradiating a catalyst precursor containing the titanium oxide in which a content of rutile type titanium oxide is 50% by mole or more and the divalent copper compound carried on a surface of the titanium oxide described above with light preferably in an atmosphere containing nitrogen and alcohol to reduce a part of the divalent copper compound to the monovalent copper compound.

<<Catalyst Precursor>>

The above catalyst precursor shall not specifically be restricted as long as it contains the titanium oxide in which a content of rutile type titanium oxide is 50% by mole or more and the divalent copper compound carried on a surface of the titanium oxide described above. For example, it may be the catalyst precursor containing only the divalent copper compound carried on a surface of the titanium oxide or may be the catalyst precursor containing the monovalent copper compound carried on a surface of the titanium oxide together with the divalent copper compound. Also, the above catalyst precursor may be such the precursor as the copper compound-carried titanium oxide photocatalyst according to the present invention in which an abundance ratio Cu(I)/[Cu(I)+Cu(II)] of the monovalent copper described above is reduced for some reason, and in this case, the present production example can be used as a method for reproducing the copper compound-carried titanium oxide photocatalyst according to the present invention.

In one example of a production process for the above catalyst precursor, a suspension is first produced by the same step as the step of preparing the suspension described above. Then, the suspension is stirred on the condition of, for example, pH 9 or higher at 60° C. or higher, preferably 70 to 100° C. and more preferably 80 to 95° C. for several hours, preferably about 1 hour without adding the reducing agent described above, and the resulting solid matter is obtained by filtering, washed with water and then dried. Thus, the catalyst precursor can be prepared.

The titanium oxide has to contain rutile type titanium oxide in a proportion of 50% by mole or more. A proportion of less than 50% by mole makes it impossible to reduce well a part of the divalent copper compound to the monovalent copper compound in a reducing step described later.

<<Reducing Step>>

In the present step, the catalyst precursor described above is irradiated with light preferably under a nitrogen and alcohol-containing atmosphere to reduce a part of the divalent copper compound contained in the catalyst precursor to the monovalent copper compound.

That is, when electrons in the titanium oxide are photoexcited by irradiation with light, the photoexcited electrons reduce divalent copper (Cu(II)) to monovalent copper (Cu(I)). Also, holes produced by the photoexcitation are consumed for decomposing the alcohol and therefore inhibited from being recombined with the photoexcited electrons. A part of the divalent copper compound is considered to be capable of being reduced well to the monovalent copper compound in the manner described above.

The alcohol described above includes preferably ethanol, methanol, 2-propanol, denatured alcohols and the like.

A content of the alcohol in the atmosphere is preferably 1 to 30% by volume, more preferably 2 to 20% by volume and further preferably 3 to 15% by volume. If it is 1% by volume or more, a part of the divalent copper compound can be reduced well to the monovalent copper compound.

The light used in irradiation with light may be a visible light or a UV ray. In irradiation with the visible light, capable of being used are lights which are emitted from light sources such as sunlight, mercury lamps, xenon lamps, white fluorescent lamps, LED and the like and which pass through an L-42 optical filter (manufactured by AGC Techno Glass Co., Ltd.). In irradiation with the UV ray, any one of sunlight, mercury lamps, xenon lamps, black lights and white fluorescent lamps can be used.

The copper compound-carried titanium oxide photocatalyst obtained by the method described above comprises composite particles in which the monovalent copper compound and the divalent copper compound are carried on a surface of the titanium oxide particles, and it is provided with a viral inactivation property and a photocatalytic activity in combination.

Use Form of Copper Compound-Carried Titanium Oxide Photocatalyst:

A use form of the copper compound-carried titanium oxide photocatalyst of the present invention shall not specifically be restricted, and it is filled, for example, in a suitable vessel in a solid form such as a fine powder, a granule and the like and can be used as it is, or it can be used in a form in which the copper compound-carried titanium oxide photocatalyst is contained in one or both of a surface and an inside of an optional base material. In general, the latter form is preferred.

Capable of being listed as the base material are, for example, base materials comprising conventional single members such as metals, ceramics, glasses and the like and composite base materials comprising two or more kinds of members, but it shall not be restricted to them. Also, the copper compound-carried titanium oxide photocatalyst may be contained in a coating agent which is releasable by suitable means such as floor polish. Further, the copper compound-carried titanium oxide photocatalyst can be fixed on a membrane and exposed on a surface of a continuous membrane. Or, capable of being used as well is the film-like copper compound-carried titanium oxide photocatalyst obtained by sputtering the copper compound-carried titanium oxide photocatalyst in a thin film form on a surface of thin film-like titanium oxide prepared by sputtering titanium oxide on glass.

In general, materials obtained by fixing the copper compound-carried titanium oxide photocatalyst on a base material surface by a fixing means such as a binder and the like can be listed as a material obtained by fixing the copper compound-carried titanium oxide photocatalyst on a base material surface. Either organic binders or inorganic binders may be used as the binder, and the inorganic binders are preferably used in order to avoid decomposition of the binder caused by photocatalytic substances. The kind of the binder shall not specifically be restricted, and capable of being used are, for example, optional binders such as polymer binders which can form a thin film by polymerization and volatilization of the solvents in addition to inorganic binders such as silica base binders and the like which are usually used for fixing photocatalytic substances on a base material surface.

Materials which can be obtained by curing dispersions prepared by dispersing the copper compound-carried titanium oxide photocatalyst described above in resins can be listed as a material containing the copper compound-carried titanium oxide photocatalyst in an inside of a base material. Either natural resins or synthetic resins may be used as the resins. Capable of being listed are, for example, acrylic resins, phenol resins, polyurethane resins, acrylonitrile/styrene copolymer resins, acrylonitrile/butadiene/styrene (ABS) copolymer resins, polyester resins, epoxy resins and the like, but they shall not be restricted to the above specific resins.

An application form of the copper compound-carried titanium oxide photocatalyst of the present invention shall not specifically be restricted, and it can be used not only under the presence of optional lights but also in dark places. Also, the copper compound-carried titanium oxide photocatalyst of the present invention has a high viral inactivation ability as well under the presence of water (for example, in water and seawater), in a dry state (for example, a state of a low humidity in a winter season) and a state of a high humidity or under the coexistence of organic substances, and it can inactivate continuously viruses. It can be applied to, for example, walls, floors, ceilings and the like, and in addition thereto, optional objects such as buildings of hospitals, factories and the like, machine tools and measuring equipments, insides and parts of electric appliances (insides of refrigerators, washing machines, dish washers and the like, filters of air cleaners and the like). The suitable examples of the dark places include applications thereof to insides of machines, storage rooms of refrigerators and hospital facilities (waiting rooms, operation rooms and the like) which are dark places in the night or in non-use, but they shall not be restricted to the above examples. Also, proposed are, for example, products in which a ceramic filter and a non-woven fabric filter of an air cleaner are coated with titanium oxide as one of measures for influenza and in which a light source for irradiating with a UV ray is mounted, but a light source of a UV ray is made dispensable by applying the copper compound-carried titanium oxide photocatalyst of the present invention to the filters, and it becomes possible to reduce the cost and enhance the safety.

EXAMPLES

The present invention shall more specifically be explained below with reference to examples, but the present invention shall not be restricted to the following examples.

Example 1

Rutile type titanium oxide 50 g (F-10, BET specific surface area: 12 $m^2/g$, manufactured by Showa Titanium K.K.) was suspended in 1000 mL of distilled water, and 0.293 g of $CuCl_2.2H_2O$ (manufactured by Kanto Chemical Co., Inc.) was added thereto so that the copper ions accounted for 0.22 part by mass based on 100 parts by mass of the titanium oxide. The suspension was heated up to 90° C. and subjected to heat treatment for 1 hour while stirring. A sodium hydroxide (manufactured by Kanto Chemical Co., Inc.) aqueous solution of 1 mol/L and 13.75 ml and a glucose (manufactured by Kanto Chemical Co., Inc.) aqueous solution of 1 mol/L and 6.88 ml were added to the above solution so that a mole ratio of $CuCl_2.2H_2O:C_6H_{12}O_6$:NaOH was 1:4:8, and the mixture was subjected to heat treatment at 70° C. for 1 hour. The slurry was filtered, and a powder obtained was washed with purified water, dried at 80° C. and crushed by means of a mixer to obtain a sample.

The sample thus obtained was heated in a hydrofluoric acid solution and totally dissolved, and the extract was quantitatively determined by ICP. As a result thereof, the copper ions accounted for 0.22 part by mass based on 100 parts by mass of the titanium oxide. That is, a whole amount of the charged copper ions (originating in $CuCl_2.2H_2O$) was carried on a surface of the titanium oxide.

In the examples and the comparative examples, the BET specific surface area was measured by means of a fully automatic BET specific surface area-measuring equipment (Macsorb, HM model-1208) manufactured by Mountech Co., Ltd.

Example 2

Rutile type titanium oxide 50 g (F-10, BET specific surface area: 12 $m^2/g$, manufactured by Showa Titanium K.K.) was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. A sodium hydroxide (manufactured by Kanto Chemical Co., Inc.) aqueous solution of 1 mol/L and 6.88 ml and a glucose (manufactured by Kanto Chemical Co., Inc.) aqueous solution of 1 mol/L and 6.88 ml were added to the above suspension so that a mole ratio of $CuCl_2.2H_2O:C_6H_{12}O_6$:NaOH was 1:4:4, and the mixture was subjected to heat treatment at 70° C. for 1 hour. The slurry was filtered, and a powder obtained was washed with purified water, dried at 80° C. and crushed by means of a mixer to obtain a sample.

Example 3

Rutile type titanium oxide 50 g (F-10, BET specific surface area: 12 $m^2/g$, manufactured by Showa Titanium K.K.) was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. A sodium hydroxide (manufactured by Kanto Chemical Co., Inc.) aqueous solution of 1 mol/L and 3.44 ml and a glucose (manufactured by Kanto Chemical Co., Inc.) aqueous solution of 1 mol/L and 6.88 ml were added to the above suspension so that a mole ratio of $CuCl_2.2H_2O:C_6H_{12}O_6$:NaOH was 1:4:2, and the mixture was subjected to heat treatment at 70° C. for 1 hour. The slurry was filtrated, and a powder obtained was washed with purified water, dried at 80° C. and crushed by means of a mixer to obtain a sample.

Example 4

Rutile type titanium oxide 50 g (F-10, BET specific surface area: 12 $m^2/g$, manufactured by Showa Titanium K.K.) was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. A glucose (manufactured by Kanto Chemical Co., Inc.) aqueous solution of 1 mol/L and 6.88 ml was added to the above suspension so that a mole ratio of $CuCl_2.2H_2O:C_6H_{12}O_6$:NaOH was 1:4:0, and the mixture was subjected to heat treatment at 70° C. for 1 hour. The slurry was filtrated, and a powder obtained was washed with purified water, dried at 80° C. and crushed by means of a mixer to obtain a sample.

Example 5

Rutile type titanium oxide (MT-150A, BET specific surface area: 100 $m^2/g$, manufactured by TAYCA CORPORATION) was calcined at 950° C. for 3 hours in an electric furnace. Then, it was crushed to obtain a crushed product (hereinafter referred to as "a MT-150A calcined product"). A BET specific surface area of the above MT-150A calcined product was measured to find that it was 5.3 $m^2/g$.

The MT-150A calcined product 50 g described above was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. A sodium hydroxide (manufactured by Kanto Chemical Co., Inc.) aqueous solution of 1 mol/L and 13.75 ml and a glucose (manufactured by Kanto Chemical Co., Inc.) aqueous solution of 1 mol/L and 6.88 ml were added to the above suspension so that a mole ratio of $CuCl_2.2H_2O:C_6H_{12}O_6$:NaOH was 1:4:8, and the mixture was subjected to heat treatment at 70° C. for 1 hour. The slurry was filtrated, and a powder obtained was washed with purified water, dried at 80° C. and crushed by means of a mixer to obtain a sample.

Comparative Example 1

Anatase type titanium oxide 50 g (FP-6, BET specific surface area: 99 $m^2/g$, manufactured by Showa Titanium K.K.) was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. A sodium hydroxide (manufactured by Kanto Chemical Co., Inc.) aqueous solution of 1 mol/L and 13.75 ml and a glucose (manufactured by Kanto Chemical Co., Inc.) aqueous solution of 1 mol/L and 6.88 ml were added to the above suspension so that a mole ratio of $CuCl_2.2H_2O:C_6H_{12}O_6$:NaOH was 1:4:8, and the mixture was subjected to heat treatment at 70° C. for 1 hour. The slurry was filtrated, and a powder obtained was washed with purified water, dried at 80° C. and crushed by means of a mixer to obtain a sample.

Comparative Example 2

Brookite type titanium oxide 50 g (NTB-01, BET specific surface area: 160 m$^2$/g, manufactured by Showa Titanium K.K.) was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. A sodium hydroxide (manufactured by Kanto Chemical Co., Inc.) aqueous solution of 1 mol/L and 13.75 ml and a glucose (manufactured by Kanto Chemical Co., Inc.) aqueous solution of 1 mol/L and 6.88 ml were added to the above suspension so that a mole ratio of $CuCl_2.2H_2O:C_6H_{12}O_6:NaOH$ was 1:4:8, and the mixture was subjected to heat treatment at 70° C. for 1 hour. The slurry was filtrated, and a powder obtained was washed with purified water, dried at 80° C. and crushed by means of a mixer to obtain a sample.

Comparative Example 3

Rutile type titanium oxide 50 g (F-10, BET specific surface area: 12 m$^2$/g, manufactured by Showa Titanium K.K.) was suspended in 1000 mL of distilled water, and 0.293 g of $CuCl_2.2H_2O$ (manufactured by Kanto Chemical Co., Inc.) was added thereto. The suspension was heated up to 90° C. and subjected to heat treatment for 1 hour while stirring. The slurry was filtrated, and a powder obtained was washed with purified water, dried at 80° C. and crushed by means of a mixer to obtain a sample.

Comparative Example 4

Rutile type titanium oxide 50 g (F-10, BET specific surface area: 12 m$^2$/g, manufactured by Showa Titanium K.K.) was suspended in 1000 mL of distilled water. $CuCl_2.2H_2O$ (manufactured by Kanto Chemical Co., Inc.) 0.293 g, a sodium hydroxide (manufactured by Kanto Chemical Co., Inc.) aqueous solution of 1 mol/L and 13.75 ml and a glucose (manufactured by Kanto Chemical Co., Inc.) aqueous solution of 1 mol/L and 6.88 ml were added to the above suspension so that a mole ratio of $CuCl_2.2H_2O:C_6H_{12}O_6:NaOH$ was 1:4:8, and the mixture was heated up to 70° C. while stirring and subjected to heat treatment for 1 hour. The slurry was filtrated, and a powder obtained was washed with purified water, dried at 80° C. and crushed by means of a mixer to obtain a sample.

<Measurements>
<<Measurement of Rutile Content in Raw Material Titanium Oxide>>

A content of rutile type titanium oxide in the raw material titanium oxides described above (F-10, MT-150A, FP-6 and NTB-01) was measured by a powder X-ray diffraction method.

That is, dried raw material titanium oxide was used and subjected to X-ray diffraction measurement on the conditions of an X-ray tube voltage of 45 kV, an X-ray tube current of 40 mA, a measuring range of 2θ=20 to 80 deg, a sampling amplitude of 0.0167 deg and a scanning rate of 1.1 deg/ minute by means of "X'pert PRO" manufactured by PANanalytical B.V. as a measuring equipment using a copper target and a Cu—Kα1 ray.

A peak height (Hr) corresponding to a rutile type crystal, a peak height (Hb) corresponding to a brookite type crystal and a peak height (Ha) corresponding to an anatase type crystal were determined, and a content (rutile content) of the rutile type titanium oxide in the titanium oxide was determined according to the following calculation formula:

Rutile content (mole %)={$Hr/(Ha+Hb+Hr)$}×100

<<Quantitative Determination of Abundance Ratio (Mole %) of Monovalent Copper (Cu(I)) and Divalent Copper (Cu(II))>>

(1) Measuring Equipment and Measuring Method:

A beam line BL14B2 in a large synchrotron radiation facility (SPring-8) of Japan Synchrotron Radiation Research Institute was used as a measuring equipment to measure an X-ray absorption near-edge fine structure (hereinafter abbreviated as "XANES") spectrum of a Cu—K shell absorption edge.

When measuring the samples obtained in the examples and the comparative example, a fluorescence method was used as the measuring method, and a transmission method was used for measuring the other samples. To be specific, a fluorescence method-measuring unit or a transmission method-measuring unit installed in the beam line BL14B2 of SPring-8 was used.

(2) Measurement of XANES Spectra of Samples Obtained in Examples and Comparative Example:

The respective samples obtained in the examples and the comparative examples were mixed with BN (boron nitride, manufactured by Kanto Chemical Co., Inc.) so that a ratio of the sample to BN was 1:1 in terms of a mass, and the mixture was pelletized by means of a disc molding equipment.

Figure 1:
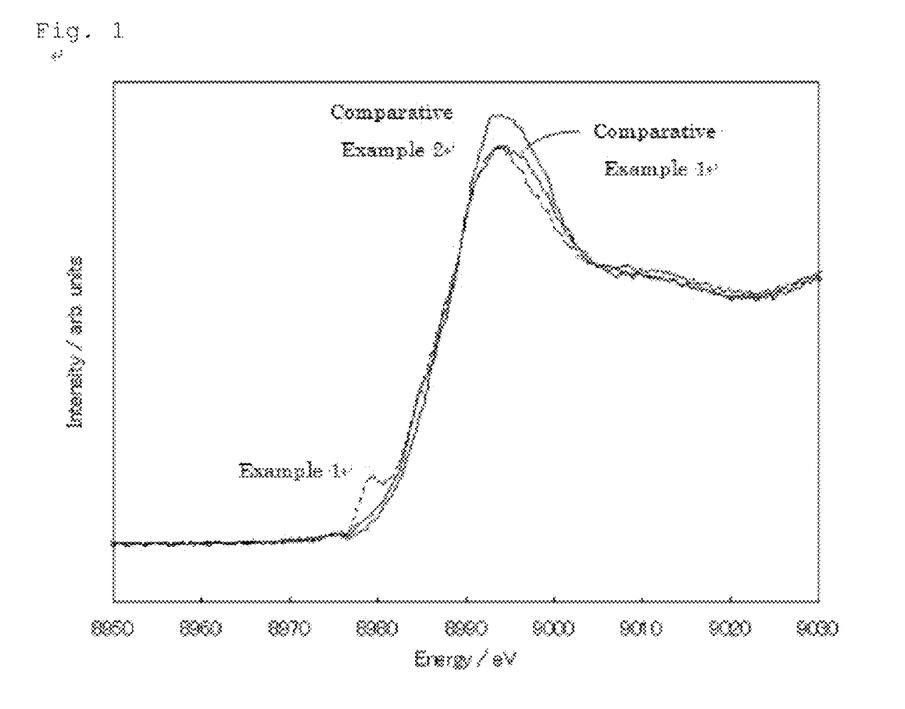
FIG. 1 is a graph showing Cu—K shell XANES spectra in Example 1 and Comparative Examples 1 to 2.

The XANES spectra of the pellets obtained above were measured. Measured results obtained in Example 1, Comparative Example 1 and Comparative Example 2 are shown in FIG. 1. In FIG. 1, peaks appearing in the vicinity of 8975 to 8980 eV are derived from Cu(I), and peaks present in the vicinity of 8990 to 8995 eV are derived from both of Cu(I) and Cu(II).

(3) Identification of Copper Compound in Sample:

CuO, $Cu_2O$, $Cu(OH)_2$ and metal Cu were mixed respectively with a prescribed amount of BN to prepare mixtures so that when pellets having a thickness of 0.5 mm were prepared from the above mixtures, they had an absorption coefficient μt of 1, and the mixtures were pelletized by means of a disc molding equipment to measure the XANES spectra of the pellets. Then, the above spectra were compared with the XANES spectra (particularly the peaks appearing in the vicinity of 8975 to 8980 eV and the vicinity of 8990 to 8995 eV) which were obtained in (1) described above by measuring the samples prepared in the examples and the comparative examples.

As a result thereof, it has been found that the copper compounds contained in the above samples are present in the forms of $Cu_2O$ and $Cu(OH)_2$.

(4) Preparation of Calibration Curve:

Then, mixtures 1 to 6 obtained by mixing $Cu_2O$ and $Cu(OH)_2$ in different mixing ratios were prepared. That is, prepared were the mixtures 1 to 6 obtained by mixing $Cu_2O$ and $Cu(OH)_2$ so that an abundance ratio {Cu(I)/(Cu(I)+Cu(II))} (mole %) of monovalent copper Cu(I) to a total amount of monovalent copper and divalent copper Cu(II) was as shown below.

Mixture 1: 0% by mole
Mixture 2: 25.4% by mole
Mixture 3: 47.6% by mole
Mixture 4: 67.2% by mole
Mixture 5: 84.5% by mole
Mixture 6: 100% by mole The above mixtures 1 to 6 were mixed with a prescribed amount of BN to prepare mixtures so that when pellets having a thickness of 0.5 mm were prepared from the mixtures prepared above, they had an absorption coefficient μt of 1, and the mixtures prepared above were pelletized by means of a disc molding equipment to prepare reference samples 1 to 6 and measure XANES spectra thereof. In this connection, the absorption coefficient μt can be determined by the following formula:

$$\mu t = \ln(I_0/I)$$

μ: linear absorption coefficient
t: thickness of the reference sample
$I_0$: X-ray intensity before entering the reference sample
I: X-ray intensity after transmitting the reference sample In the respective reference samples 1 to 6, a value obtained by dividing, as shown in the following formula, an intensity of a pre-edge peak derived from Cu(I) which appeared in the vicinity of 8977 eV by a maximum intensity of peaks in the spectra present in the vicinity of 8990 to 8995 eV was determined as a normalized value.

$$\text{normalized value} = (\text{intensity of pre-edge peak})/(\text{maximum intensity})$$

Accordingly, it is shown that the larger the above normalized value is, the larger the abundance ratio {Cu(I)/(Cu(I)+Cu(II))} (mole %) of Cu(I) is.

Figure 2:
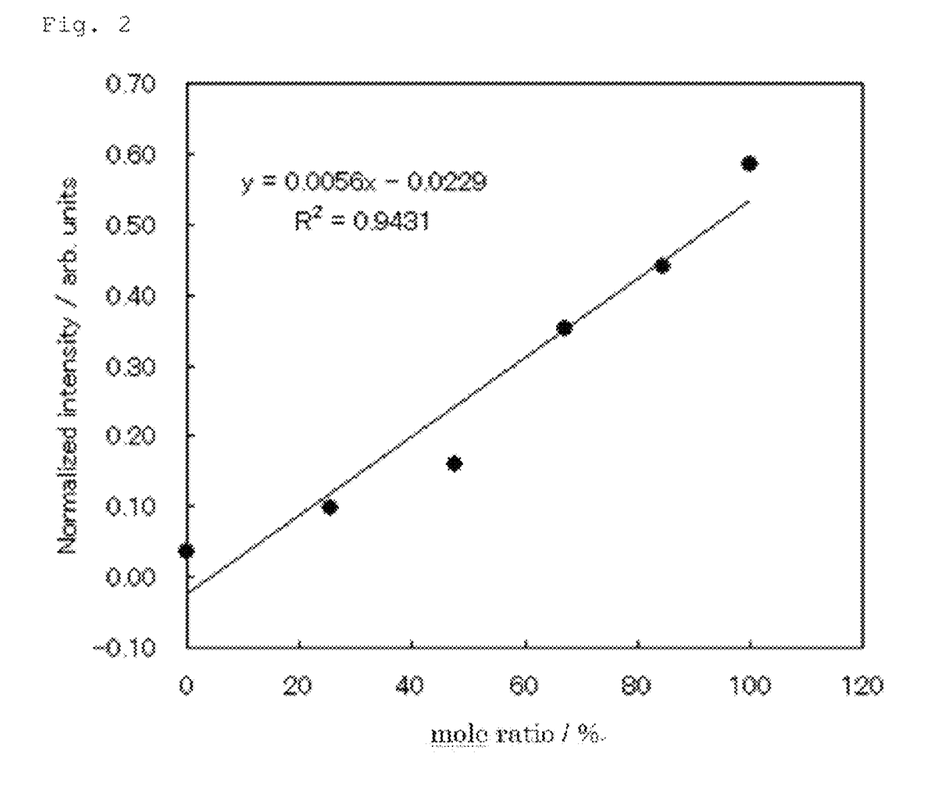
FIG. 2 is a calibration curve showing relation between an abundance ratio of Cu(I) and a normalized value of a Cu—K shell XANES spectrum in the reference samples 1 to 6.

As shown in FIG. 2, the data (mole ratios and normalized values) of the reference samples 1 to 6 were plotted in a graph in which the abundance ratio of Cu(I) described above was allotted to an axis of abscissa and in which the normalized value described above was allotted to an axis of ordinate, and a linear equation was determined by a least squares method to prepare a calibration curve.

(5) Quantitative Determination of Abundance Ratios of Cu(I) and Cu(II) in the Respective Samples:

In the samples obtained in the examples and the comparative examples, the normalized values described above were determined from the XANES spectra measured in (2), and the calibration curve prepared in (4) described above was used to determine the abundance ratios (mole %) of Cu(I) and Cu(II) described above. The results thereof are shown in Table 1.

<<Evaluation of Volatile Organic Compound (VOC) Decomposition Activity: Measurement of $CO_2$ Generation Amount>>

A glass-made petri dish having a diameter of 1.5 cm was disposed in a closed type glass-made reaction vessel (capacity: 0.5 L), and 0.3 g of the samples obtained in the examples and the comparative examples was put on the above petri dish. The reaction vessel was substituted in an inside thereof with a mixed gas having a volume ratio of 1:4 of oxygen to nitrogen and charged with 5.2 μL of water (corresponding to a relative humidity of 50% (25° C.)) and 5.0 mL of a 5.1 volume % acetaldehyde standard gas (mixed gas with nitrogen, standard state (25° C., 1 atm)) (acetaldehyde concentration in the glass-made reaction vessel was set to 500 ppm by volume), and the reaction vessel was irradiated from an outside thereof with a visible light.

Figure 3:
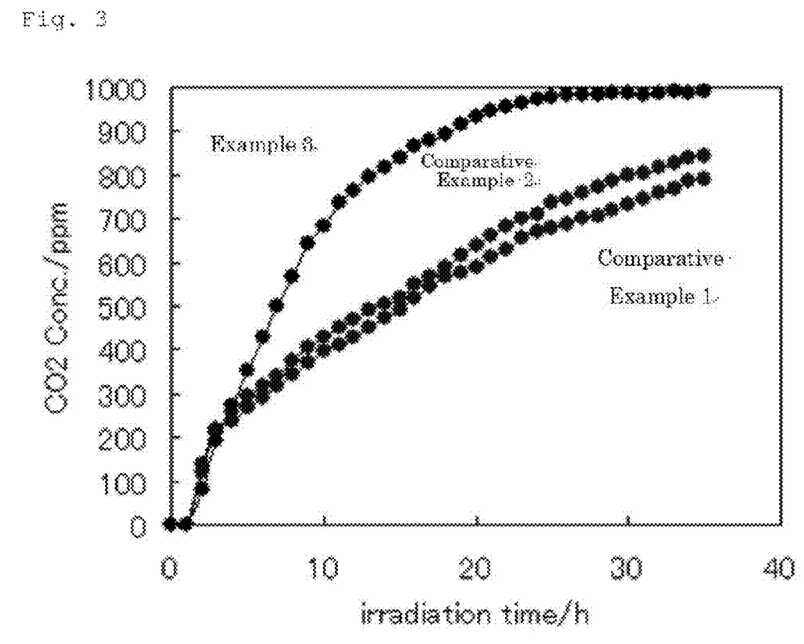
FIG. 3 is a graph showing a change of a generation amount of $CO_2$ with time in the samples prepared in Example 3 and Comparative Examples 1 to 2.

A xenon lamp equipped with a filter (trade name: L-42, manufactured by AGC TECHNO GLASS CO., LTD.) for cutting a UV ray having a wavelength of 400 nm or less was used as a light source for irradiation with a visible light, and it was set in a position in which an illuminance in the reaction vessel was 100,000 lux. A reducing rate of acetaldehyde and a generating rate of carbon dioxide which was an oxidative decomposition product were measured with the passage of time by gas chromatography. A generating amount (ppm by mass) of $CO_2$ observed when 1 hour passed since irradiation with a visible light is shown in Table 1. Also, the measured results of the samples prepared in Example 3, Comparative Example 1 and Comparative Example 2 are shown in FIG. 3.

<<Evaluation of Viral Inactivation Ability: Measurement of $LOG(N/N_0)$>>

The viral inactivation ability was confirmed by the following method according to a model experiment using bacteriophage. A method for making use of an inactivation ability to bacteriophage as a model for a viral inactivation ability is described in, for example, Appl. Microbial Biotechnol., 79, pp. 127 to 133, 2008, and it is known that reliable results are obtained.

A filter paper was spread in a deep petri dish, and a small amount of sterilized water was added thereto. A glass-made stand having a thickness of about 5 mm was put on the filter paper, and a glass plate (50 mm×50 mm×1 mm) coated with 1.5 mg of the samples obtained in the examples and the comparative examples was put thereon. A QB phage (NBRC20012) suspension 100 μL which was acclimatized in advance and had a known concentration was dropwise added thereon, and an OHP film was covered thereon in order to bring a surface of the sample into contact with the phage. The above deep petri dish was covered with a glass plate to prepare a set for measurement. A plurality of the same sets for measurement was prepared.

Used as a light source was a 15 W white fluorescent lamp (full white fluorescent lamp FL15N, manufactured by Panasonic Corporation) equipped with a UV ray cut filter (KU-1000100, manufactured by King Works Co., Ltd.), and a plurality of the sets for measurement was left standing still in a position in which the luminance (measured by an illuminometer: TOPCON IM-5) was 800 lux. A phage concentration of the sample on the glass plate was measured after prescribed time passed.

The phage concentration was measured by the following method. The sample on the glass plate was dipped in 10 mL of a recovering liquid (SM Buffer) and shaken for 10 minutes by means of a shaker. The above phage recovering liquid was suitably diluted and mixed with a culture solution ($OD_{600}$>1.0, 1×10$^8$ CFU/mL) of colon bacilli (NBRC13965) which was cultured separately, and the mixture was stirred. Then, it was left standing still for 10 minutes in a thermostatic chamber of 37° C. to infect the colon bacilli with the phages. This liquid was spread on an agar medium to culture the phages at 37° C. for 15 hours, and then a plaque number of the phages was visually measured. The plaque number thus obtained was multiplied by a dilution rate of the phage recovering liquid to thereby determine a phage concentration N thereof.

Figure 4:
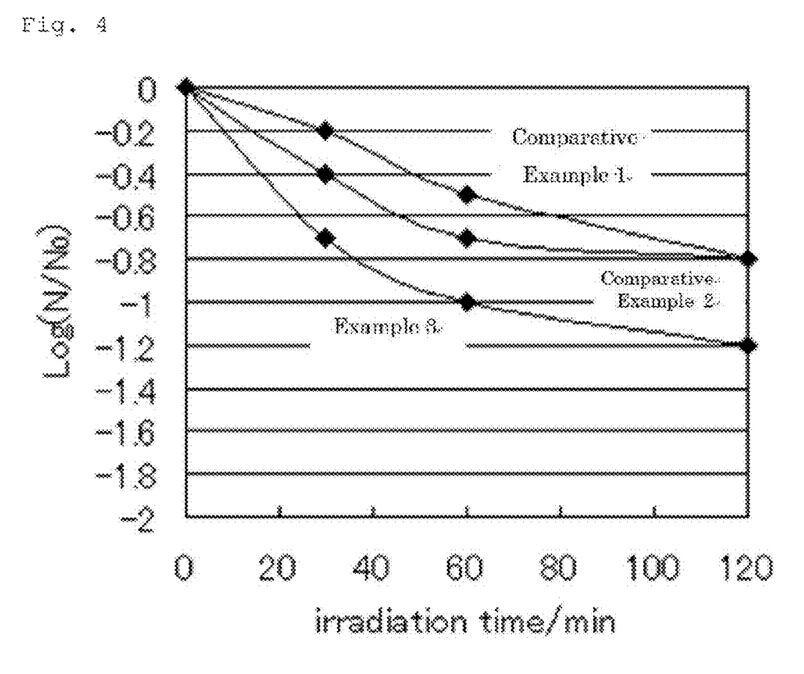
FIG. 4 is a graph showing a change of a phage relative concentration (LOG ($N/N_0$)) with time in the samples prepared in Example 3 and Comparative Examples 1 to 2.

The phage relative concentration ($LOG(N/N_0)$) was determined from the initial phage concentration $N_0$ and the phage concentration N after prescribed time passed. The results thereof are shown in Table 1 and FIG. 4.

TABLE 1

| | TiO₂ | | Slurry | | | XANES measuring results | | Viral inactivation property | Photocatalytic activity CO₂ generation amount |
| | | Rutile content | | Others (mole ratio) | | Abundance ratio of Cu(I) | Abundance ratio of Cu(II) | | |
| | Kind | (mole %) | TiO₂ (g) | CuCl₂•2H₂O  C₆H₁₂O₆  NaOH | | (%) | (%) | LOG (N/N₀) (2 h irradiation) | (1 h) (ppm) |
|---|---|---|---|---|---|---|---|---|---|
| Example 1 | F-10 | 85 | 50 | 1  4  8 | | 34 | 66 | −3.7 | 70 |
| Example 2 | F-10 | 85 | 50 | 1  4  4 | | 28 | 72 | −3.3 | 74 |
| Example 3 | F-10 | 85 | 50 | 1  4  2 | | 13 | 87 | −1.2 | 80 |
| Example 4 | F-10 | 85 | 50 | 1  4  0 | | 12 | 88 | −1.0 | 81 |
| Example 5 | MT-150A burned product | 100 | 50 | 1  4  8 | | 56 | 44 | −4.1 | 88 |
| Comparative Example 1 | FP-6 | 5 | 50 | 1  4  8 | | 14 | 86 | −0.8 | 46 |
| Comparative Example 2 | NTB-01 | 0 | 50 | 1  4  8 | | 13 | 87 | −0.8 | 51 |
| Comparative Example 3 | F-10 | 85 | 50 | 1  0  0 | | 0 | 100 | −0.7 | 86 |
| Comparative Example 4 | F-10 | 85 | 50 | 1  4  8 | | 100 | 0 | −4.5 | 35 |

<Results>

In Example 3 (principal component: rutile type titanium oxide), Comparative Example 1 (principal component: anatase type titanium oxide) and Comparative Example 2 (principal component: brookite type titanium oxide), an abundance ratio of copper (I) contained in the titanium oxide photocatalyst powders obtained is approximately the same (13 to 14%). It is shown by comparison of the $CO_2$ generation amounts that the highest generation amount is observed in Example 3 (principal component: rutile type titanium oxide). This shows that the photocatalytic activity (photoexcitation degradability) exerted by a visible light is improved by using titanium oxide comprising rutile type titanium oxide as a principal component.

The photocatalysts prepared in Examples 1 to 5 contain both of Cu(I) and Cu(II) and therefore are excellent in both of an antiviral property (LOG(N/N₀)) and a photocatalytic activity ($CO_2$ generation amount). Also, the photocatalysts prepared in Examples 1 to 4 are higher in this order in an abundance ratio of Cu(II), and therefore they are more excellent in this order in a photocatalytic activity ($CO_2$ generation amount) exerted by a visible light. On the contrary, the photocatalysts prepared in Examples 4, 3, 2 and 1 are higher in this order in an abundance ratio of Cu(I), and therefore they are more excellent in this order in a viral inactivation property. In Example 5, an abundance ratio of Cu(I) is higher than in Examples 1 to 4, and therefore the viral inactivation property is more excellent than in Examples 1 to 4. Though an abundance ratio of Cu(II) is lower in Example 5 than in Examples 1 to 4, the photocatalytic activity is more excellent than in Examples 1 to 4. It is considered as one of the reasons therefor that a content (100% by mole) of rutile type titanium oxide contained in the titanium oxide is higher in Example 5 than in Examples 1 to 4 (85% by mole).

In Example 1 (principal component: rutile type titanium oxide), Comparative Example 1 (principal component: anatase type titanium oxide) and Comparative Example 2 (principal component: brookite type titanium oxide), the same procedure was carried out, except that the different titanium oxide raw materials were used. Comparison of an abundance ratio of Cu(I) in the samples obtained shows that it is the highest in Example 1 (principal component: rutile type titanium oxide). This shows that a method in which the titanium oxide comprising rutile type titanium oxide as a principal component is used to produce the copper compound-carried titanium oxide photocatalyst is suitable for enhancing an abundance ratio of Cu(I) for the purpose of improving an antiviral property and the like.

Example 6

Rutile type titanium oxide 50 g (F-10, BET specific surface area: 12 m²/g, manufactured by Showa Titanium K.K.) was suspended in 1000 mL of distilled water, and 0.293 g of CuCl₂.2H₂O (manufactured by Kanto Chemical Co., Inc.) was added thereto. The suspension was heated up to 90° C. and subjected to heat treatment for 1 hour while stirring. The slurry was filtrated, and a powder obtained was washed with purified water, dried at 80° C. and crushed by means of a mixer to obtain a sample A.

A mixture prepared by mixing the sample A described above with BN in a ratio of 1:1 in terms of a mass ratio was molded by means of a disc molding equipment to prepare pellets having a thickness of 0.5 mm. The pellets prepared and a filter paper impregnated with 1 g of ethanol were put in a Tedlar bag, and an atmosphere in an inside of the Tedlar bag was substituted with nitrogen.

Figure 5:
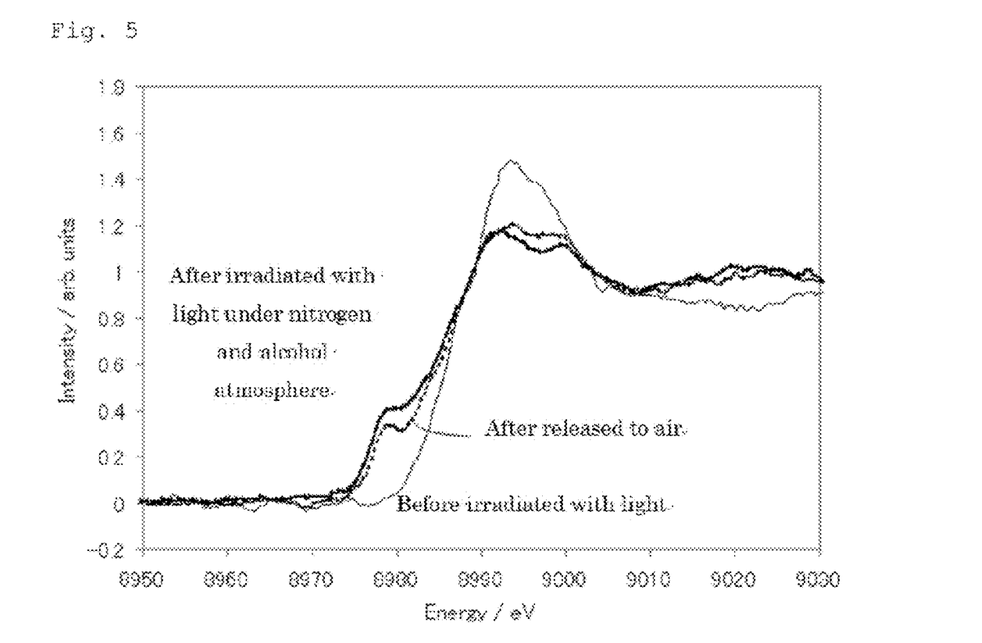
FIG. 5 is a graph showing a change of Cu—K shell XANES spectra obtained when rutile type titanium oxide carried thereon with a divalent copper compound is irradiated with light under a nitrogen and ethanol atmosphere.

Next, the reaction vessel was irradiated from an outside thereof with a visible light according to the following procedure, and a XANES spectrum of the pellets was measured by a fluorescence method. That is, a XANES spectrum of the copper compound-carried titanium oxide was measured under a nitrogen and alcohol-containing atmosphere while irradiating with a visible light (100000 lux) for 30 minutes, and then the light was cut off to measure (30 minutes) a XANES spectrum of the sample of the copper compound-carried titanium oxide released from the Tedlar bag to the air. The results thereof are shown in FIG. 5 and Table 2.

Also, 0.3 g of the sample A (not mixed with BN) described above and a filter paper impregnated with ethanol were put in a 500 mL glass vessel and irradiated with a visible light (100000 lux) for a night. Cu(I) was produced on a surface of the titanium oxide by the above operation. Then, the reaction vessel was substituted in an inside thereof with a mixed gas having a volume ratio of 1:4 of oxygen to nitrogen and charged with 5.2 μL of water (corresponding to a relative humidity of 50% (25° C.)) and 5.0 mL of a 5.1 volume % acetaldehyde standard gas (mixed gas with nitrogen, standard state (25° C., 1 atm)) (acetaldehyde concentration in the glass-made reaction vessel was set to 500 ppm by volume), and the reaction vessel was irradiated from an outside thereof with a visible light (100000 lux). An amount of $CO_2$ produced by irradiation for 1 hour is shown in Table 2.

Comparative Example 5

Figure 6:
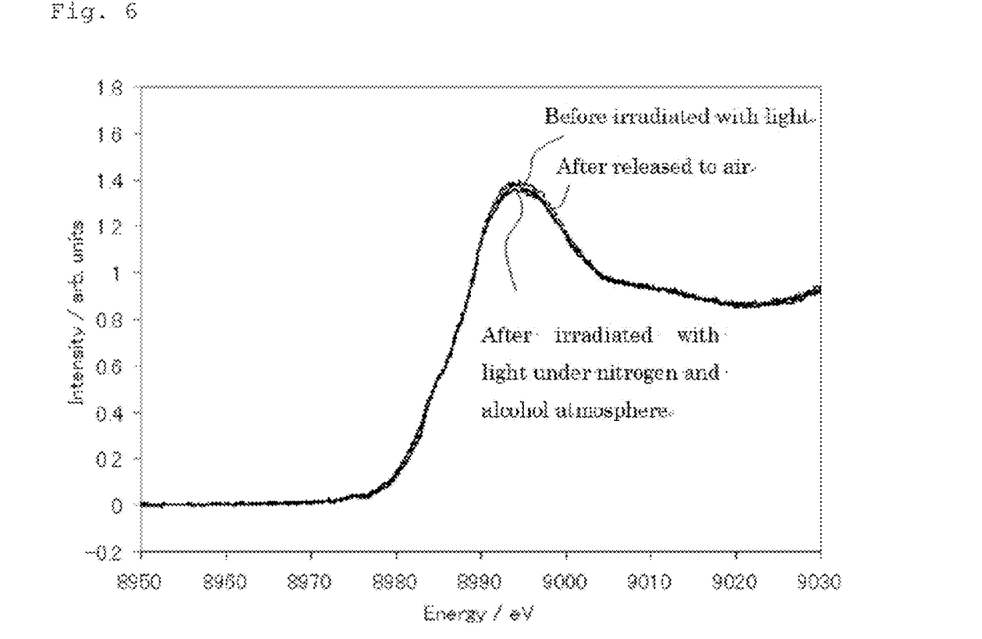
FIG. 6 is a graph showing a change of Cu—K shell XANES spectra obtained when anatase type titanium oxide carried thereon with a divalent copper compound is irradiated with light under a nitrogen and ethanol atmosphere.

The same operation as in Example 6 was carried out, except that anatase type titanium oxide (FP-6, BET specific surface area: 99 $m^2/g$, manufactured by Showa Titanium K.K.) was used in place of the rutile type titanium oxide. The results thereof are shown in FIG. 6 and Table 2.

Comparative Example 6

Figure 7:
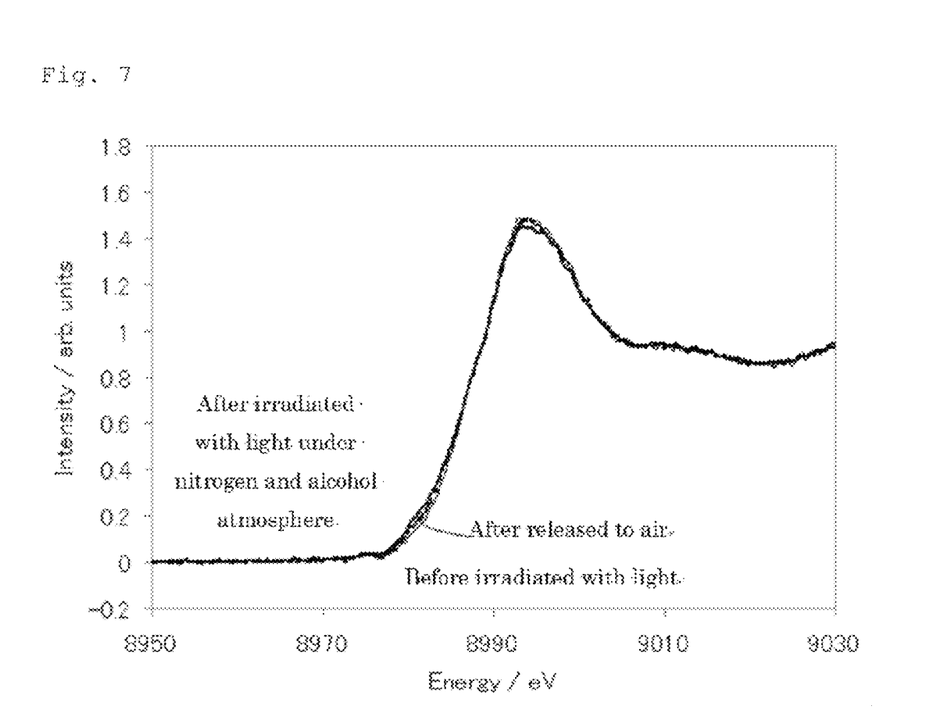
FIG. 7 is a graph showing a change of Cu—K shell XANES spectra obtained when brookite type titanium oxide carried thereon with a divalent copper compound is irradiated with light under a nitrogen and ethanol atmosphere.

The same operation as in Example 6 was carried out, except that brookite type titanium oxide (NTB-01, BET specific surface area: 160 $m^2/g$, manufactured by Showa Titanium K.K.) was used in place of the rutile type titanium oxide. The results thereof are shown in FIG. 7 and Table 2.

TABLE 2

| | Titanium oxide | | Pellet (mixture of Sample A and BN) Cu(I)/{Cu(I) + Cu(II)} (mole %) | | | Sample A $CO_2$ generation |
|---|---|---|---|---|---|---|
| | Kind | Principal component | Rutile content (mole %) | Before irradiated with light | After irradiated with light | After released to air | amount (1 h) (ppm) |
| Example 6 | F-10 | Rutile type | 85 | 0 | 67 | 54 | 163 |
| Comparative Example 5 | FP-6 | Anatase type | 5 | 0 | 1 | 0 | 26 |
| Comparative Example 6 | NTB-01 | Brookite type | 0 | 0 | 2 | 0 | 30 |

<Results>

The pellets comprising the rutile type titanium oxide as a principal component in Example 6 were as high as 67% by mole in an amount of Cu(I) produced by a visible light and quick in a reduction rate from Cu(II) to Cu(I). Also, the sample A comprising the rutile type titanium oxide as a principal component in Example 6 was as high as 163 ppm by mass in a production amount of $CO_2$. The reason why a production amount of $CO_2$ was raised as described above is considered to be attributable to that holes produced by reduction from Cu(II) to Cu(I) decomposed efficiently acetaldehyde.

In contrast with this, the pellets prepared in Comparative Examples 5 and 6 in which the rutile type titanium oxide was not a principal component were slow in a reduction rate from Cu(II) to Cu(I) and small in a production amount of $CO_2$ as compared with the pellets and the sample A prepared in Examples 6.

The above results show that rutile type titanium oxide is excellent in a regenerative ability from Cu(II) to Cu(I) and a photoinduced degradability as compared with anatase type titanium oxide and brookite type titanium oxide.

What is claimed is:

1. A copper compound carried on a titanium oxide photocatalyst comprising titanium oxide in which a content of rutile type titanium oxide is 80% by mole or more and a monovalent copper compound and a divalent copper compound which are carried on a surface of said titanium oxide,
    wherein an abundance ratio of monovalent copper to a sum of monovalent copper and divalent copper is 20 to 70% by mole.

2. The copper compound carried on a titanium oxide photocatalyst according to claim 1, wherein the monovalent copper compound contains copper (I) oxide.

3. The copper compound carried on a titanium oxide photocatalyst according to claim 1, wherein the divalent copper compound contains copper (II) hydroxide.

4. The copper compound carried on a titanium oxide photocatalyst according to claim 1, wherein the titanium oxide described above is obtained by a vapor phase method.

5. A production process for a copper compound carried on a titanium oxide photocatalyst, comprising a step of depositing a monovalent copper compound and a divalent copper compound on a surface of titanium oxide in which a content of rutile type titanium oxide is 80% by mole or more,
    wherein an abundance ratio of monovalent copper to a sum of monovalent copper and divalent copper is 20 to 70% by mole.

6. The production process for a copper compound carried on a titanium oxide photocatalyst according to claim 5, comprising a step of adding a reducing agent for reducing divalent copper to monovalent copper to a suspension prepared by blending the divalent copper compound with the titanium oxide in which a content of rutile type titanium oxide is 50% by mole or more.

7. The production process for a copper compound carried on a titanium oxide photocatalyst according to claim 5, comprising a step of irradiating a catalyst precursor containing the titanium oxide in which a content of rutile type titanium oxide is 50% by mole or more and the divalent copper compound carried on a surface of the titanium oxide described above with light to reduce a part of the divalent copper compound to the monovalent copper compound.

8. The production process for a copper compound carried on a titanium oxide photocatalyst according to claim 7, wherein the irradiation with light described above is carried out in an alcohol-containing atmosphere.

9. The production process for a copper compound carried on a titanium oxide photocatalyst according to claim 5, wherein the titanium oxide described above is obtained by a vapor phase method.

* * * * *